(12) United States Patent
Chen et al.

(10) Patent No.: US 8,830,469 B2
(45) Date of Patent: Sep. 9, 2014

(54) METHOD FOR DETECTION OF GASES BY LASER SPECTROSCOPY, AND GAS SENSOR

(75) Inventors: Jia Chen, München (DE); Andreas Hangauer, München (DE); Rainer Strzoda, München (DE)

(73) Assignee: Siemens Aktiengesellschaft, Munich (DE)

( * ) Notice: Subject to any disclaimer, the term of this patent is extended or adjusted under 35 U.S.C. 154(b) by 598 days.

(21) Appl. No.: 13/003,464

(22) PCT Filed: Jul. 1, 2009

(86) PCT No.: PCT/EP2009/058255
§ 371 (c)(1),
(2), (4) Date: Apr. 1, 2011

(87) PCT Pub. No.: WO2010/003857
PCT Pub. Date: Jan. 14, 2010

(65) Prior Publication Data
US 2011/0181879 A1    Jul. 28, 2011

(30) Foreign Application Priority Data
Jul. 9, 2008  (EP) .................................... 08012398

(51) Int. Cl.
*G01N 21/00* (2006.01)
*G01N 21/39* (2006.01)
*G01N 21/27* (2006.01)
*G01N 21/35* (2014.01)

(52) U.S. Cl.
CPC .......... *G01N 21/39* (2013.01); *G01N 2021/399* (2013.01); *G01N 21/3504* (2013.01); *G01N 21/274* (2013.01); *G01N 2201/127* (2013.01)

USPC .......... 356/437; 356/318; 356/435; 356/128; 356/237.2; 250/345; 73/23.31

(58) Field of Classification Search
USPC ......................................... 356/437, 632, 128
See application file for complete search history.

(56) References Cited

U.S. PATENT DOCUMENTS 4,489,239 A * 12/1984 Grant et al. ............... 250/339.03
4,924,095 A * 5/1990 Swanson, Jr. ............... 250/338.5
5,184,241 A * 2/1993 Schwemmer ................... 398/93

(Continued)

FOREIGN PATENT DOCUMENTS

WO    2006/030058    3/2006
WO    2006/130014    12/2006

*Primary Examiner* — Tarifur Chowdhury
*Assistant Examiner* — Isiaka Akanbi
(74) *Attorney, Agent, or Firm* — Cozen O'Connor

(57) ABSTRACT

A method and a sensor for detecting a target gas by laser spectroscopy using a laser or a laser diode having a monochrome emission wavelength that can be modulated by varying the operating temperature or the operating current. The wavelength range of the target gas comprises a first modulation of the laser or the laser diode over a first large modulation width, in addition to at least two absorption lines of a reference gas and at least one absorption line of the target gas. The absorption lines are used to calibrate the wavelength scale of the laser or the laser diode in relation to the varied operating temperature or operating current, a second modulation of the laser or the laser diode being performed over a second small modulation width, with the at least one absorption line of the target gas, for detecting the target gas.

11 Claims, 3 Drawing Sheets

(56) References Cited

U.S. PATENT DOCUMENTS

| | | |
|---|---|---|
| 5,500,768 A | 3/1996 | Doggett et al. |
| 5,877,862 A * | 3/1999 | Nelson et al. ............... 356/436 |
| 6,631,019 B1 * | 10/2003 | Vujkovic-Cvijin et al. .. 398/195 |
| 6,822,742 B1 * | 11/2004 | Kalayeh et al. ............... 356/437 |
| 2005/0134859 A1 * | 6/2005 | Kalayeh et al. ............... 356/437 |

* cited by examiner

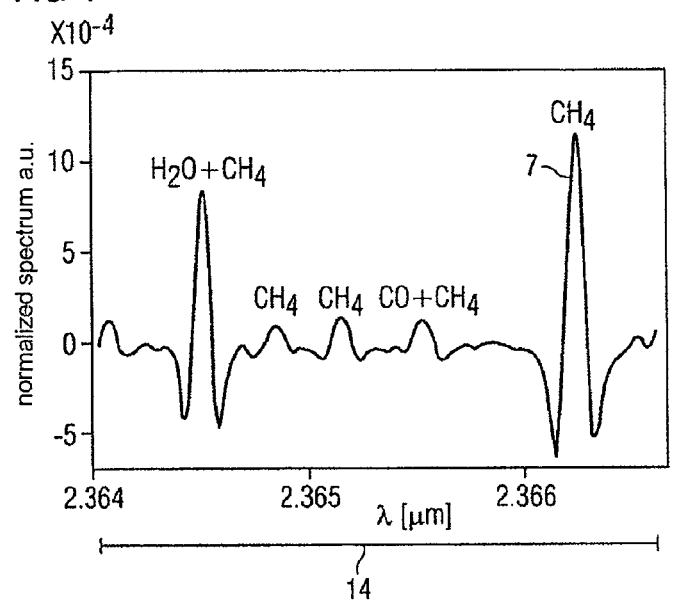
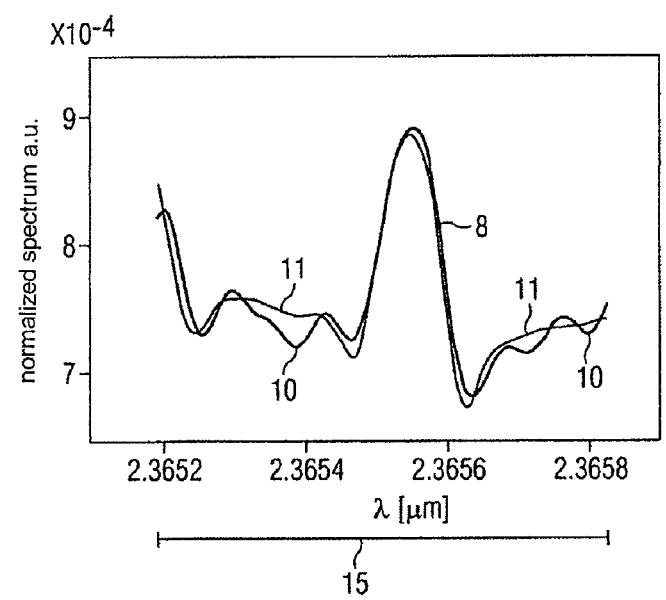

METHOD FOR DETECTION OF GASES BY LASER SPECTROSCOPY, AND GAS SENSOR

CROSS-REFERENCE TO RELATED APPLICATIONS

This is a U.S. national stage of International Application No. PCT/EP2009/058255, filed on 1 Jul. 2009. This patent application claims the priority of European patent application EP 08012398 filed 9 Jul. 2008, the entire content of which application is incorporated herein by reference in its entirety.

BACKGROUND OF THE INVENTION

1. Field of the Invention

The invention relates to detecting gases and, more particularly, to a method for detecting gases, using laser-spectroscopic methods. Specifically, a light source with monochromatic light is used, i.e., a laser or a laser diode, as well as an absorption path or measurement cell, a photodetector, and electronics for controlling the measurement process and for evaluation. The spectral tuning capability of the light source of the laser diode makes it possible to record absorption spectra. The monochromatic form of, for example, a laser diode is necessary to allow the individual vibration/rotation transitions of the gas molecules to be resolved without broadening because of the principle used. In general, a measurement is performed on an absorption measurement path which contains at least one measurement gas or target gas.

2. Description of the Related Art

Carbon monoxide (CO) is, for example, a target gas to be determined. This occurs in the event of incomplete combustion in furnace installations, in engines or in the event of fires. In the building field, a considerable risk with a fatal outcome can occur as a consequence of combustion gases being accidentally misdirected. However, the risk of poisoning can be precluded by monitoring rooms where there is a hazard of toxic carbon dioxide or carbon monoxide concentrations.

For example, if a smoke alarm is equipped with an additional carbon monoxide detector, then this considerably improves the reliability of fire identification. In applications such as this, in which absolute detection reliability is required, human life may depend on the serviceability of corresponding sensors.

Previously known carbon monoxide detection methods already use absorption spectroscopy using tunable laser diodes. The abbreviation for this method is TDLS, Tunable Diode Laser Spectroscopy, with a tunable laser diode or laser.

Such methods have the following characteristic features. An absolute measurement is possible, and a corresponding sensor is resistant to dirt. The spectral measurement over an absorption line of a gas always also includes the background, where the ratio between the minimum transmission of the absorption line and background transmission is proportional to the gas concentration. An absolute change in the transmission, such as due to a window becoming dirty, does not influence the concentration measurement. Normally, light attenuation can rise by several orders of magnitude before the sensor noise increases significantly.

No appliance constants occur in conjunction with the apparatuses that are used. Because of the narrow spectral width of the laser emission, the measured spectra can be compared directly with theoretical spectra without any further instrument function, based simply on molecule constants and physical variables such as pressure, temperature and optical wavelength.

The above-described technique allows a measurement to be performed which is stable in the long term. The measurement principle which is based on fundamental physics, in conjunction with the abovementioned characteristics of the measurement method, allow a gas monitor to be produced which is stable in the long term.

Self-monitoring is performed inherently. Permanent absorption with a reference gas allows continuous monitoring of the serviceability of the sensor.

Malfunctions, such as an escape of the reference gas, interruption in the optical path, a defect in a laser or in a laser diode or in electrical components, can thus be detected immediately.

The maximum possible selectivity is self-evident, because the individual absorption lines of a gas have a narrow bandwidth. As a result, each gas generally has a spectral fingerprint which cannot be confused. The high-resolution measurement with precise detection of individual lines therefore allows extremely selective concentration determination.

Laser spectroscopy using a tunable laser diode generally allows a measurement without any delay, which is highly useful, in particular for exhaust-gas measurements for regulatory purposes.

Furthermore, a series of conventional detection principles are known for verification of carbon dioxide, such as metal oxide sensors, electrochemical cells, color change with synthetic hemoglobin or infrared photometry. By way of example, electrochemical cells play a major role for monitoring room air. However, one disadvantage is that electrochemical cells cannot check their own serviceability. It is therefore necessary after an operating life of several years to ensure that the sensor is still performing a correct measurement, and the serviceability must be regularly tested using a test gas. A carbon monoxide monitor based on TDLS allows self-monitoring.

TDLS-based carbon monoxide detection is used in the professional environment, for example, for monitoring safety at work. Here, not only are the procurement costs significant, but also the running costs, such as for regular checks. Furthermore, freedom from maintenance is an important factor. Fields of use for laser spectroscopy with a tunable laser diode may include fire identification in buildings, in aircraft and in marine vessels, and the control and monitoring of furnace installations, as well as an early indicator of malfunctions in internal combustion engines.

Fundamentally, there are two options for the tuning of tunable laser diodes. Tuning by the temperature of the laser diode, linked to a specific subarea of a spectrum, is relatively slow. If the laser diode is tuned by variation of the operating current, then this is achieved more quickly than in the case of the abovementioned method. In general, the wavelength scale for tuning a laser diode cannot, however, be considered to be linear. That is, the precise structure of the spectrum covered is unknown. Furthermore, a gas to be detected, such as carbon monoxide, is not present in the atmosphere. As a result, the gas is not detected.

SUMMARY OF THE INVENTION

It is therefore an object of the invention to reliably confirm identification of each of the individual absorption lines in a spectrum which is covered by a tunable laser diode or a laser, with respect to the operating temperature or the operating current. In addition, it is an object to provide a sensor which is not subject to drift phenomena or ageing phenomena during its life.

When absorption spectra are measured using tunable lasers or laser diodes, the problem exists that the emission wavelengths of the laser or of the laser diode is not known sufficiently clearly for accurate evaluation of the spectra. The method of the invention overcomes this disadvantage and is implemented using laser diodes which can be tuned widely by the current, with the aim of covering at least 0.5 nm when tuning for a spectral measurement. The further development of electronic components, such as laser diodes, normally results in further examples with more extensive emission wavelength ranges. It is essential for TDLS technology, laser spectroscopy with a tunable laser diode, that different types of laser diodes can be used. The correct choice for a specific method is dependent on a large number of parameters. It is essential that a monochromatic light source is available, that an absorption path is provided, and that a photodetector and electronics are provided for controlling the measurement process and the evaluation.

The method of the invention eliminates the disadvantage that, for example, although a laser diode can be tuned within specific ranges, i.e., by the operating current, there is, however, initially no reliable correlation with individual spectral lines. In order to calibrate the wavelength scale of a diode relative to the operating current, when tuning the laser diode in a broad wavelength range of the wavelength scale, the laser diode is tuned, for example, over at least 0.5 nanometers. This tuning range is spectrally positioned such that not only are at least two or more known absorption lines of the reference gas covered thereby, but also possibly known absorption lines of the target gas are covered. The wavelength scale of the diode can therefore be calibrated reliably, thus resulting in an accurate association between the operating current and the emission wavelength within the extremely narrow frequency tuning range.

Since latest developments have introduced so-called vertically emitting laser diodes, i.e., vertical cavity surface emitting lasers (VCSEL), which, for example, allow detection of CO at a wavelength of 2.3 µm, this cutting-edge data extends the TDSL technology in the direction of reliability and speed. It is therefore advantageously possible to use a vertically emitting laser diode which, for example, emits monochromatic light at 2.3 µm, and which can furthermore cover a spectrum of at least up to 3.0 or 4.0 nanometers, by variation of the operating current.

A reference gas which is used for the measurement can advantageously be accommodated directly in a reference gas cell in the main beam path. By way of example, this can be located in the same housing as the photodetector. The measurement gas cell and the reference gas cell are therefore connected in series in the beam path between the laser diode and the photodetector. In accordance with the present method, the reference gas can be used without any loss of reliability. The reference gas and target gas should, however, be different.

It is advantageous for a target gas to always be present in the atmosphere, and for the at least one absorption line of a reference gas to be replaced by at least one absorption line of the at least one target gas.

If an absorption spectrum from tuning over the second narrow tuning width is compared with a calculated absorption spectrum, using non-iterative curve matching with a linear regression algorithm, then the concentration of the at least one target gas can be calculated particularly quickly, in one step.

A reference gas cell can easily be connected in series with the photodetector and the absorption path, if the reference gas does not correspond to the target gas.

Other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims. It should be further understood that the drawings are not necessarily drawn to scale and that, unless otherwise indicated, they are merely intended to conceptually illustrate the structures and procedures described herein.

BRIEF DESCRIPTION OF THE DRAWINGS

Exemplary embodiments which do not restrict the invention will be described in the following text with reference to schematic figures, in which:

FIG. 1 shows a graphical plot of a wavelength-differentiated spectrum with individual absorption lines, as a representative for specific gases; the absorption lines of methane can be used to calibrate the spectrum and the operating current;

FIG. 2 shows a graphical plot of the wavelength range of a narrow wavelength range associated with FIG. 1, in which at least one absorption line of the target gas, in this case carbon monoxide CO, is located;

DETAILED DESCRIPTION OF THE PREFERRED EMBODIMENT

Because of the wide tuning range of vertical cavity surface emitting lasers (VCSEL), a considerable' spectrum width can be covered for wavelength identification, for example at least 0.5 nm (VCSEL at 760 nm) to 4.0 nm (VCSEL at≥2 µm). The time period for recording a corresponding spectrum may, for example, be 640 ms. Apart from the relatively wide scanning range, as shown in FIG. 1, the wavelength scale is extracted based on the known position of strong absorption lines, such as the methane line 7. This results in an accurate association between the operating current, which is varied in order to tune the laser diode, relative to the respective wavelength in the spectrum.

FIG. 2 shows a graphical plot of an absorption line 8 of a target gas, in this case carbon monoxide (CO). The tuning range illustrated in FIG. 2, with respect to the wavelength, is contained in the wavelength range illustrated in FIG. 1, or forms a subset. The calibration based on FIG. 1, provided it is performed for each measurement of a target gas, thus allows extremely precise detection of, for example, carbon monoxide. In particular, it is possible to use lasers or laser diodes which can be tuned such that at least one absorption line of carbon monoxide and at least three of methane are covered as a reference gas, and which can be tuned in or over a range of, for example, 4.0 nm in the wavelength. A preliminary calibration can thus be performed without any problems for each target-gas-oriented measurement, as shown in FIG. 2, by a measurement, corresponding to FIG. 1, with a greater frequency spectrum covered and a second narrow tuning width 15, such that the frequency scale is calibrated and no inaccuracies relating to the position of spectral lines occur in the evaluation.

Figure 3:
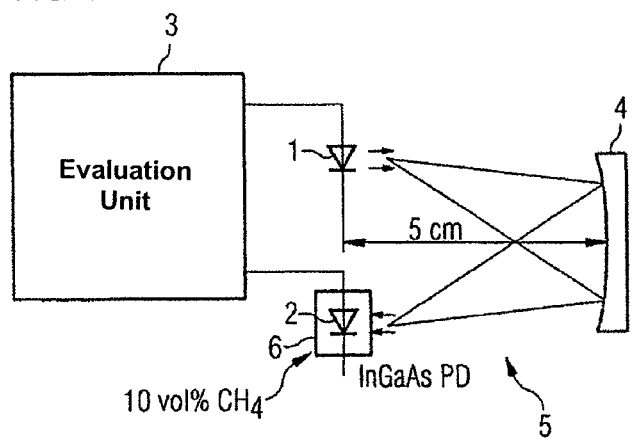
FIG. 3 shows a schematic block diagram of the configuration of a carbon monoxide sensor with the reference gas cell and an evaluation unit, and in particular with an integrated measurement cell and the laser diode as a transmitter.

As shown in FIG. 3, a housing for the photodetector 2 is in the form of a reference gas cell 6 in which case, by way of example, there are 10% by volume of methane ($CH_4$) in the housing of the photodetector 2. By way of example, the photodetector 2 may consist of an InGaAs diode. The entire illustration, corresponding to FIG. 3, can be accommodated in a housing which is not illustrated in any more detail, with an evaluation unit 3 being connected, which is used to control and to evaluate corresponding methods. By way of example, a spherical mirror 4 is combined with the measurement cell 5. As a result, the beam path of the beams emitted by the laser diode 1 falls on the photodetector 2 at least after passing twice through the absorption path.

The actual detection and determination of the gas concentration comprises a spectral measurement over a broad and a narrow wavelength range, corresponding to FIGS. 1 and 2. The broad, first tuning width 14 is used for wavelength identification, i.e., for determining the wavelength tuning response of the laser with the current. This response cannot be expected to be constant over the life of the laser. Consequently, the broad tuning width 14, corresponding to FIG. 1, is repeated at suitable intervals for permanent calibration, in order to guarantee the reliability of the measurement of carbon monoxide. The identification of the absorption lines is a pattern recognition process, and operates reliably for all gas compositions.

Efficient, linear curve matching can be performed with precise knowledge of the wavelength scale, during the recording of a specific range in a spectrum. This is based on the scaling of the gas concentration of the spectrum. The concentration of carbon monoxide (CO) and of methane ($CH_4$), as well as an offset, are described in the examples described here. The model spectrum is calculated analytically, based on the tabular line parameters, after each tuning with a broad spectral range. The linear correspondence is implemented as a scalar product which can be calculated, where, for example, measurement rates of 10 Hz, in each case with complete curve matching, are performed on a 24 MHz microprocessor in the present sensor. However, the measurement rate may also be higher than the value stated here. The present method is faster by one to two orders of magnitude than previously known iterative, so-called "curve fit" methods without detailed knowledge of the wavelength scale. By way of example, carbon monoxide is detected reliably using a carbon monoxide sensor with an integration time of 100 ms. A sufficiently short measurement time can be ensured for reliable detection of the maximum workplace concentration (MWC) value. Carbon monoxide measurements in the exhaust gas of a gas burner are performed quickly and reliably. It is even possible to perform a measurement in the sub-ppm range if longer integration times are used.

In each case, the wavelengths are shown in μm on the abscissa in FIGS. 1 and 2. A normalized spectrum is plotted on the ordinate. A spectrum can be converted or shown as a function of the frequency, at any time.

FIG. 1 shows strong and weak absorption lines of methane, which is used as the reference gas. In order to calibrate a reference spectrum with respect to the tuning current of a laser or of a laser diode, it may be worthwhile to use two or three known reference gases, which are present over a broad wavelength range in a spectrum measurement, with a known absorption line for calibration. The spectrum covered and the corresponding tuning current are therefore defined precisely at two or three points. Tuning in a subarea of this broad spectrum corresponding to FIG. 1 can then be performed to detect absorption lines of the target gas 8. The curve annotated 10 in FIG. 2 corresponds to a carbon monoxide concentration measurement. The curve which has been subjected to linear curve matching has the reference symbol 11.

Here, with the absorption line 8 of carbon monoxide, the target gas differs only insignificantly with respect to these two measured and corrected curves 10, 11. In this case, a carbon monoxide concentration is present, i.e., a measurable amount of the target gas is present.

Figure 4:
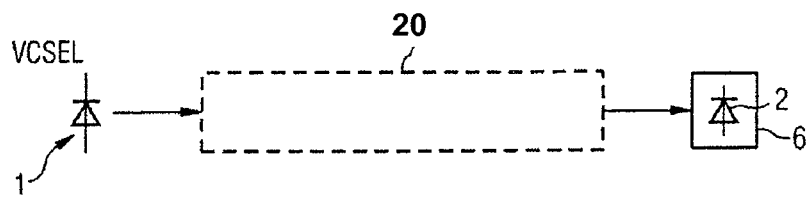
FIG. 4 shows a schematic block diagram of a sensor design with a laser diode 1, a measurement cell 5, and a reference gas cell 6 with a photodetector connected in series.

The absorption path 20 and the reference gas cell 6 can be arranged in series without any loss of reliability, provided that the reference gas does not correspond to the target gas. An arrangement such as this is shown in FIG. 4. The absorption lines 7 of the reference gas, e.g., case methane, are used as a wavelength marker. The identification scheme requires a widely tunable laser or a laser diode. This is necessary since the absorption lines of the target gas and reference gas are several nanometers apart from one another. This can clearly be seen in FIG. 1. Conventional edge-emitting semiconductor lasers can be tuned only over at most 2 nm by the operating current in the near infrared (NIR) range. The invention operates with semiconductor lasers which have a wavelength tuning range of at least 2.5 nm in the infrared range or in the NIR range. No beam splitters are required, because of the series connection corresponding to the concept described above. It is possible to use a low-cost reflective geometry with a hollow mirror 4, as shown in FIG. 3. This arrangement furthermore results in the optical path length being doubled, with the same geometric extent.

As shown in FIG. 4, the photodetector 2 is provided with a reference gas which is present in a reference gas cell 6. This instrumentation equipment is sufficient, together with optics, which are not illustrated. Overall, this saves a separate cuvette for the reference gas. The capability to use simple optics reduces the number of components that need to be used. If the target gas is not identical to the reference gas, problems in distinguishing between the measurement gas and reference gas are avoided.

Measurements have been performed with a vertically emitting laser (VCSEL). A laser which emits at a wavelength of 2.3 μm is used for a carbon monoxide monitor. A calibration can be performed using a compact optical reference gas cell 6. The sensor is therefore precisely calibrated using the concept of a broad tuning width for wavelength identification and calibration and the narrow tuning width for carbon monoxide concentration determination, throughout the entire life of the sensor which, typically, is more than ten years.

Further advantages are that malfunctions of the sensor, such as blockage of the optical path or outward diffusion of reference gas, can be reliably identified. Furthermore, laser ageing phenomena are compensated for.

The precise knowledge of the wavelength scale during the measurement, which can be achieved without an external wavelength reference or separate reference cell, allows not only an improvement in reliability but also a compact sensor design and data evaluation which is faster by several orders of magnitude. This significantly improves the requirements for the sensor for fitting with measurement instruments. The proposed concept can be used universally, and can be utilized virtually universally.

For example, it can also be used for detection of nitrogen monoxide (NO) at a wavelength in a band of about 1.8 μm, with the reference gas $H_2O$, or for the detection of water ($H_2O$) at a wavelength of 2 μm, with the reference gas $CO_2$.

The requirements for the measurement accuracy with respect to the reference gas can be less stringent for the concentration measurement.

Figure 5:
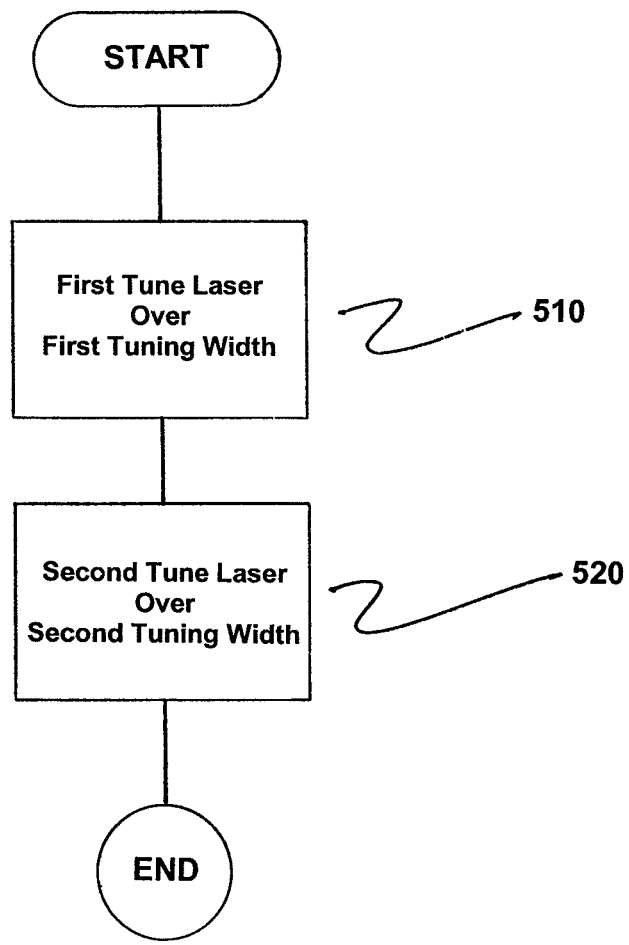
FIG. 5 is a flow chart of a method in accordance with an Embodiment of the invention.

FIG. 5 is a flow chart of a method for detecting at least one target gas by laser spectroscopy using one of a laser and a laser diode having a monochromic emission wavelength and which is tuneable by varying one of an operating temperature and operating current. The method comprises tuning of a laser or a laser diode over a first broad tuning first width in a wavelength range of a single band of the at least one target gas, as indicated in step 510.

Here, at least two absorption lines of a reference gas and at least one absorption line of the at least one target gas are included, for calibration of a wavelength scale of the laser or the laser diode relative to a varied operating temperature or a varied operating current.

The laser or the laser diode is second tuned over a second, narrow tuning width in the wavelength range of the single band of the at least one target gas, as indicated in step 520. Here, the second, narrow tuning width at which the second tuning is performed is narrower than the first broad tuning width, and at least one of the at least one absorption line of the at least one target gas is included for detection of the at least one target gas, where the target gas and reference gas are different gases.

Thus, while there are shown, described and pointed out fundamental novel features of the invention as applied to preferred embodiments thereof, it will be understood that various omissions and substitutions and changes in the form and details of the illustrated apparatus, and in its operation, may be made by those skilled in the art without departing from the spirit of the invention. Moreover, it should be recognized that structures shown and/or described in connection with any disclosed form or embodiment of the invention may be incorporated in any other disclosed or described or suggested form or embodiment as a general matter of design choice.

The invention claimed is:

1. A method for detecting at least one target gas by laser spectroscopy using one of a laser and a laser diode having a monochromic emission wavelength and which is tuneable by varying one of an operating temperature and operating current, the method comprising:
    first tuning of the one of the laser and the laser diode over a first broad tuning width in a wavelength range of one band of the at least one target gas, at least two absorption lines of a reference gas and at least one absorption line of the at least one target gas being included in the first tuning width, for calibration of a wavelength scale of the one of the laser and the laser diode relative to one of a varied operating temperature and a varied operating current;
    second tuning of the one of the laser and the laser diode over a second, narrow tuning width in the wavelength range of the one band of the at least one target gas, the second, narrow tuning width at which the second tuning is performed being narrower than the first broad tuning width, at least one of the at least one absorption line of the at least one target gas being included in the second tuning width, for detection of the at least one target gas;
    detecting the at least one gas by laser spectroscopy using the one of the laser and the laser diode; and
    measuring a concentration of the at least one target gas;
    wherein the target gas and reference gas are different gases.

2. The method as claimed in claim 1, wherein at least one of the at least two absorption lines of the reference gas is replaced by one of the at least one absorption line of the at least one target gas, if a minimum concentration of the at least one target gas is continuously present.

3. The method as claimed in claim 1, wherein at least one of the at least two absorption lines of the reference gas is replaced by one of the at least one absorption line of the at least one target gas, if a minimum concentration of the at least one target gas is continuously present.

4. The method as claimed in claim 1, wherein a measurement cell and a reference gas cell are connected in series in a beam path of the one of the laser and the laser diode.

5. The method as claimed in claim 1, wherein the first tuning is performed for calibration of one of the operating current and the operating temperature using an absolute wavelength scale, and the second tuning is successively performed for a plurality of times to detect the at least one target gas.

6. The method as claimed in claim 1, wherein an absorption spectrum during the second tuning over the second, narrow tuning width is compared with a calculated absorption spectrum, and wherein non-iterative curve matching is used with a linear regression algorithm to allow calculation of a concentration of the at least one target gas in a single step.

7. A sensor for detection of at least one target gas by laser spectroscopy, the sensor comprising:
    a measurement cell;
    an evaluation unit;
    one of a laser and a laser diode having a monochromic emission wavelength and which is tuneable by varying one of an operating temperature and operating current, the one of the laser and the laser diode further having a tuning range such that at least two absorption lines of a reference gas and at least one absorption line of the at least one target gas are covered in a first, broad tuning width during a tuning process; and
    a photodetector including a housing in which a reference gas cell is accommodated and which is positioned in front of the photodetector such that the measurement cell and the reference cell gas are connected in series with respect to a beam path of the laser or laser diode;
    wherein the target gas and the reference gas are different gases;
    wherein, in addition to detecting the at least one target gas by laser spectroscopy, a concentration of the at least one target gas is measured.

8. The sensor as claimed in claim 7, wherein the laser or laser diode is tuneable by varying the operating current, and covers an emission wavelength in a band of carbon monoxide at 2.3 μm, and wherein the at least one of the laser the laser diode is tuneable over a wavelength range which allows spectrally resolved absorption measurement of reference and target gas lines.

9. The sensor as claimed in claim 7, wherein, the at least one of the laser and the laser diode is a vertically emitting laser diode.

10. The sensor as claimed in claim 7, wherein the at least one of the laser and the laser diode is tuneable over at least 0.5 nm.

11. The sensor as claimed in claim 9, wherein the vertically emitting laser diode is a vertical cavity surface emitting laser (VCSEL).

* * * * *